United States Patent [19]

Kawahara et al.

[11] Patent Number: 5,559,003
[45] Date of Patent: Sep. 24, 1996

[54] ASSAY METHOD FOR BIOLOGICAL COMPONENTS

[75] Inventors: Sumi Kawahara; Toshikatsu Abe; Kenji Hosoi, all of Tokyo, Japan

[73] Assignee: Daiichi Pure Chemicals Co., Ltd., Tokyo, Japan

[21] Appl. No.: 348,870

[22] Filed: Nov. 29, 1994

[30] Foreign Application Priority Data

Dec. 10, 1993 [JP] Japan ................. 5-310126

[51] Int. Cl.$^6$ ............... C12Q 1/28; C12Q 1/26; C12Q 1/54; G01N 33/48
[52] U.S. Cl. ............... 435/28; 435/25; 435/18; 435/17; 435/21; 435/14; 435/12; 435/11; 435/10; 435/4; 436/63; 436/14; 436/13; 436/12; 436/74; 436/71
[58] Field of Search ............... 435/28, 25, 4, 435/14, 11, 10, 18, 17, 21, 12; 436/63, 14, 13, 12, 74, 71

[56] References Cited

U.S. PATENT DOCUMENTS

| | | | |
|---|---|---|---|
| 3,886,045 | 5/1975 | Meiattini | 435/14 |
| 3,983,005 | 9/1976 | Goodhue et al. | 435/11 |
| 4,101,381 | 7/1978 | Klose et al. | 435/11 |
| 4,247,631 | 1/1981 | Nix et al. | 435/10 |
| 4,680,259 | 7/1987 | Cumbo et al. | 435/11 |
| 4,855,228 | 8/1989 | Charlton et al. | 435/28 |
| 4,892,816 | 1/1990 | Akiba et al. | 435/11 |
| 4,929,545 | 5/1990 | Freitag | 435/11 |
| 5,350,675 | 9/1994 | Makino et al. | 435/11 |
| 5,384,248 | 1/1995 | Sakata et al. | 435/25 |

FOREIGN PATENT DOCUMENTS 0402094  12/1990  European Pat. Off. .

Primary Examiner—John Kight
Assistant Examiner—Louise N. Leary
Attorney, Agent, or Firm—Bacon & Thomas

[57] ABSTRACT

The method is directed to assaying for biological components in a sample comprising step (A) generating an oxidase substrate in the presence of an amphoteric surfactant and in the absence of ferrocyanide; (B) initially generating hydrogen peroxide through said oxidase reaction on said substrate of oxidase with subsequent detection of the generated hydrogen peroxide using peroxidase and a color developer capable of being oxidized in the presence of amphoteric surfactant and ferrocyanide; and (C) correlating the amount of color developed to the amount of biological components in the biological sample. Even when the biological component to be detected is present in a very small amount, the interference of bilirubin can be eliminated in assays of biological components in which peroxidase generated from an enzymatic reaction is detected using peroxidase and a color developer capable of being oxidized.

20 Claims, 1 Drawing Sheet

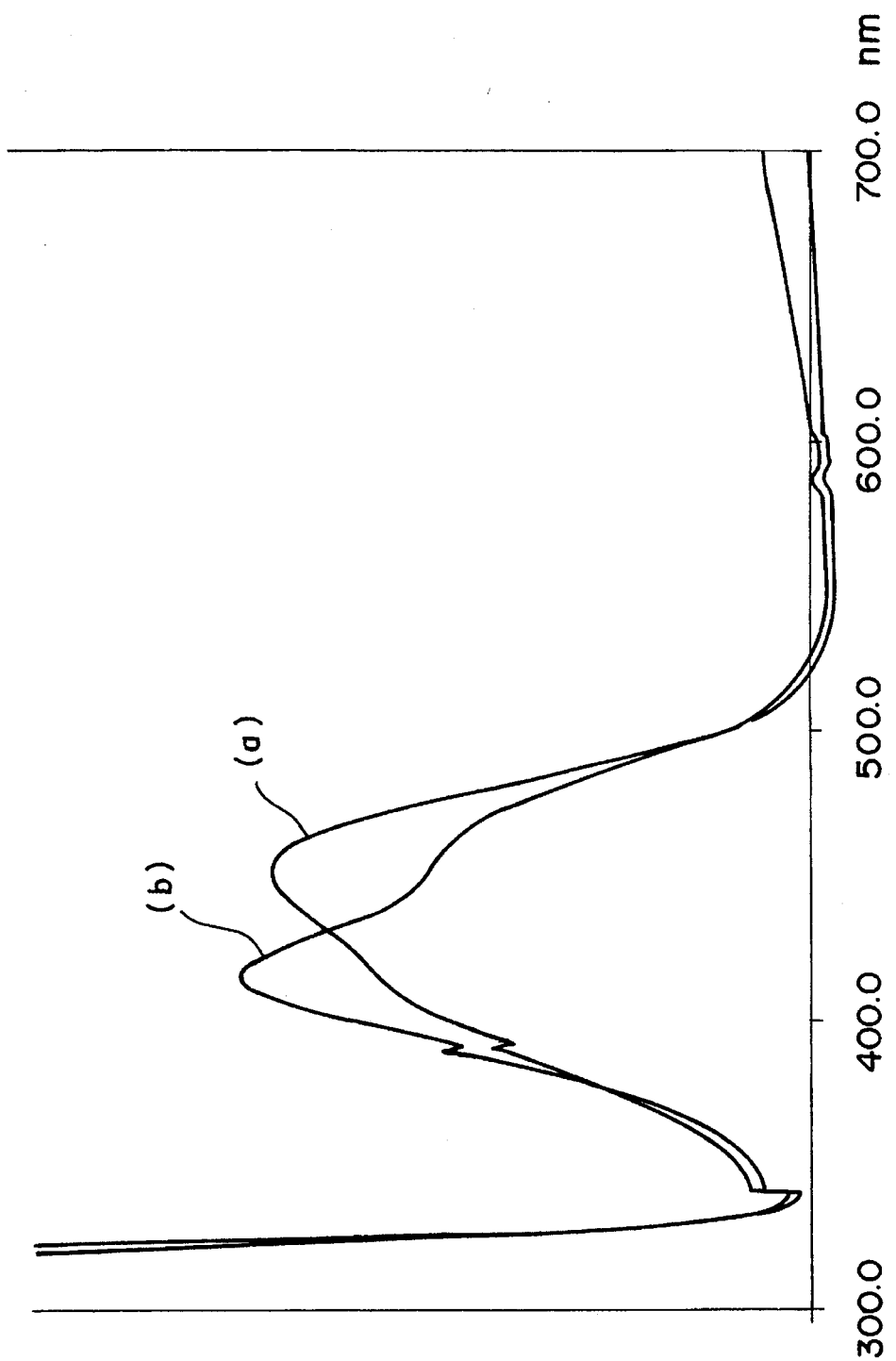

ASSAY METHOD FOR BIOLOGICAL COMPONENTS

BACKGROUND OF THE INVENTION

1. Field of the Invention

The present invention relates to an assay method for biological components which is not affected by the presence of bilirubin. More particularly, the present invention relates to an assay method for biological components which is carried out by detecting, using peroxidase and a color developer capable of being oxidized, hydrogen peroxide generated from an enzymatic reaction, and which is free from errors ascribed to bilirubin.

2. Description of Related Art

Enzymatic analyses employ enzymes as analytical reagents. They are superior to other assay methods relying on chemical reactions with respect to specificity. In addition, enzymatic reactions proceed under mild conditions. Because of these features, enzymatic analyses are easily automated, and therefore are widely used in the field of clinical chemistry.

In some cases, however, enzymatic analyses are interfered with various kinds of impurities in biological samples to an extent that cannot be neglected when precise assay is needed. In such cases, the target substance is not necessarily the only substance that is assayed. Particularly, it is known that bilirubin in biological samples affects colorimetric determination in which a suitable oxidizing enzyme is reacted with a substance to be analyzed and hydrogen peroxide generated is contacted with a reagent to develop color in the presence of peroxidase ("Japanese Journal of Clinical Chemistry", vol 8, No. 1, 63–72 (1980)). Therefore, in the determination of trace components of living bodies, interference by bilirubin is a problem which cannot be ignored.

In order to avoid the effects by bilirubin, various methods have been developed, including a bilirubin oxidase method ("Clinical Chemistry", 30/8, 1389–1392 (1984)), an aminopyrin method ("Clinical Chemistry", 27/11, 1941–1942 (1980)), a potassium ferrocyanide method ("Clinical Chemistry", 26(2), 227–231 (1980)), and an albumin-aminopyrin method (Japanese Patent Publication (kokoku) No. 4-61640). Recently, a method which employs potassium ferrocyanide and albumin in combination has also been reported (Japanese Patent Application Laid-open (kokai) No. 60-228963).

However, none of these prior methods is successful in completely eliminating interference by bilirubin, particularly when trace components are assayed. In addition, the reagents themselves have problems; i.e., they tend to become colored, or proteins contained therein are degraded.

In view of the foregoing, the inventors of the present invention carried out detailed studies and found that when an amphoteric surfactant is combined with conventional assays for biological components using ferrocyanides, interference by bilirubin can be remarkably eliminated even though the target biological component to be detected is present in only a very small amount, leading to completion of the present invention.

SUMMARY OF THE INVENTION

Accordingly, an object of the present invention is to provide an assay method for biological components in which hydrogen peroxide generated from an enzymatic reaction is detected with peroxidase and a color developer capable of being oxidized in the presence of an amphoteric surfactant and a ferrocyanide.

The above and other objects, features, and advantages of the present invention will become apparent from the following description.

BRIEF DESCRIPTION OF THE DRAWINGS

FIG. 1 shows absorption curves in the range of 300 to 700 nm in which a surfactant is added (curve (b)) or is not added (curve (a)) to bilirubin.

DESCRIPTION OF PREFERRED EMBODIMENTS

There is no particular limitation on the amphoteric surfactants which can be used in the present invention. For example, alkylimidazolium betaine, alkylbetaine, alkylamide betaine, alkylalanine, alkylamine oxide, and derivatives thereof can be used. The alkyl groups of these amphoteric surfactants each preferably have 6 to 20 carbon atoms. Specific examples of commercially available amphoteric surfactants include Anhitol 24B (alkylbetaine derivative, by Kao), Anhitol 20Y (alkylimidazolium betaine derivative, by Kao), Enagycol C-40H (alkylimidazolium betaine derivative, by Lion), Lipomin CH (alkylimidazolium betaine derivative, by Lion), Enagycol C-30B (alkylamide betaine derivative, by Lion), and Anhitol 20N (alkylamine oxide derivative, by Kao). It is preferred that the amphoteric surfactants be used from 0.01 to 10% by weight and particularly preferably from 0.1 to 5% by weight in the detection system.

The ferrocyanides used in the present invention are, for example, alkali metal ferrocyanides such as potassium ferrocyanide and sodium ferrocyanide. It is preferred that the ferrocyanides be used from 1 to 100 μM and particularly preferably from 5 to 50 μM in the detection system.

The color developers used in the present invention which can be oxidized are preferably combinations of 4-aminophenazone (particularly, 4-aminoantipyrine) and hydrogen donors such as phenols or anilines. Examples of the hydrogen-donating phenols include phenol and p-chlorophenol, and examples of the hydrogen-donating anilines include N-alkyl-N-sulfoalkyl-m-toluidine and N,N-dialkylaniline.

The assay method of the present invention is applicable to any colorimetry assay in which an enzyme is reacted with a biological component to generate hydrogen peroxide, and the hydrogen peroxide is reacted with a color developer capable of being oxidized in the presence of peroxidase. The biological components are components co-existing with bilirubin in living bodies, such as components in blood (whole blood, plasma, and serum) and urine. Specific examples of the biological components include triglyceride, glucose, phospholipids (lecithin, sphingomyelin, and lysolecithin), total cholesterol, free fatty acids, uric acid, cholinesterase, creatinine, and creatine.

The enzymes which are reacted with the biological components mentioned above are not particularly limited as long as they ultimately generate peroxide in one way or another. Specific examples of the enzymes include lipoprotein lipase, glycerokinase, glycerol-3-phosphate oxidase, glucose oxidase, phospholipase D, choline oxidase, cholesterol esterase, cholesterol oxidase, acyl CoA synthetase, acyl CoA oxidase, uricase, cholinesterase, and cholinoxidase.

Examples of enzymatic reaction systems in which the above enzymes are reacted are illustrated below.

Assay of triglyceride:

1) triglyceride $\xrightarrow{\text{lipoprotein lipase}}$ glycerol + fatty acid glycerol + ATP $\xrightleftharpoons{\text{glycerokinase}}$ glycerol-3-phosphate + ADP glycerol-3-phosphate + $O_2$ $\xrightarrow{\text{glycerol-3-phosphate oxidase}}$ dihydroxyacetone phosphate + $H_2O_2$ $2H_2O_2$ + 4-aminoantipyrine +

N-ethyl-N-sulfopropyl-m-toluidine $\xrightarrow{\text{peroxidase}}$ quinone dye (purple color) + $4H_2O$.

Assay of glucose:

2) glucose + $H_2O$ + $O_2$ $\xrightarrow{\text{glucose oxidase}}$ $H_2O_2$ + gluconic acid $2H_2O_2$ + 4-aminoantipyrine + N,N-diethylaniline +

$H^+$ $\xrightarrow{\text{peroxidase}}$ quinone dye (purple color) + $4H_2O$.

Assay of phospholipids:

3) phospholipids (lecithin, sphingomyelin, lysolecithin) $\xrightarrow{\text{phospholipase D}}$ choline + (phosphatidic acid, N-acylsphingosylphosphate, lysophosphatidic acid)

choline + $2O_2$ + $H_2O$ $\xrightarrow{\text{choline oxidase}}$ $2H_2O_2$ + betaine $2H_2O_2$ + 4-aminoantipyrine + phenol $\xrightarrow{\text{peroxidase}}$ quinone dye (red color) + $4H_2O$.

Assay of total cholesterol:

4) ester-type cholesterol + $H_2O$ $\xrightarrow{\text{cholesterol esterase}}$ free cholesterol + fatty acid free cholesterol + $O_2$ $\xrightarrow{\text{cholesterol oxidase}}$ $H_2O_2$ + Δ4-cholestenone $2H_2O_2$ + 4-aminoantipyrine + N,N-diethylaniline +

$H^+$ $\xrightarrow{\text{peroxidase}}$ quinone dye (purple color) + $4H_2O$.

Assay of free fatty acid:

5) free fatty acid + ATP + CoA $\xrightarrow[\text{Mg}^{2+}]{\text{acyl CoA synthetase}}$ acyl CoA + AMP + pyrophosphoric acid acyl CoA + $O_2$ $\xrightarrow{\text{acyl CoA oxidase}}$ 2,3-transenol CoA + $H_2O_2$ $2H_2O_2$ + 4-aminoantipyrine + N-ethyl-N-sulfopropyl-m-toluidine +

$H^+$ $\xrightarrow{\text{peroxidase}}$ quinone dye + $4H_2O$.

Assay of uric acid:

6) uric acid + $O_2$ + $2H_2O$ $\xrightarrow{\text{uricase}}$ allantoin + $CO_2$ + $H_2O_2$ $2H_2O_2$ + 4-aminoantipyrine +

N-ethyl-N-sulfopropyl-m-toluidine + $H^+$ $\xrightarrow{\text{peroxidase}}$ quinone dye + $4H_2O$.

Assay of cholinesterase:

7) benzoylcholine + $H_2O$ $\xrightarrow{\text{cholinesterase}}$ choline + benzoic acid choline + $2O_2$ + $H_2O$ $\xrightarrow{\text{choline oxidase}}$ $2H_2O_2$ + betaine $2H_2O_2$ + 4-aminoantipyrine + phenol $\xrightarrow{\text{peroxidase}}$ quinone dye.

Assay of creatinine:

8) creatinine + $H_2O$ $\xrightarrow{\text{creatininase}}$ creatine creatine + $H_2O$ $\xrightarrow{\text{creatinase}}$ sarcosine + urea sarcosine + $H_2O$ + $O_2$ $\xrightarrow{\text{sarcosine oxidase}}$ glycine + HCHO + $H_2O_2$ $\xrightarrow{\text{peroxidase}}$ quinone dye.

Needless to say, in reactions in which a biological component is reacted with an enzyme as shown by the above schemes, coenzymes and substrates can be used as desired.

Upon completion of the enzymatic reaction for generating hydrogen peroxide and the subsequent reaction for detecting the hydrogen peroxide generated, the amount of the dyes generated is determined to precisely measure the amount of the target biological component.

EXAMPLES

The present invention will further be described by way of examples, which should not be construed as limiting the invention.

REFERENCE EXAMPLE 1

FIG. 1 shows an absorption curve of bilirubin (curve (a)), and an absorption curve of bilirubin to which an amphoteric surfactant is added (curve (b)).

In detail, curve (a) depicts absorption when 2.6 ml of a buffer was added to 70 μl of a bilirubin solution, whereas curve (b) depicts absorption when 2.6 ml of a buffer containing 0.39% by weight of laurylbetaine was added to 70 μl of a bilirubin solution, both in the range from 300 to 700 nm.

As is apparent from FIG. 1, the absorption curve of bilirubin (a) shifts to a peculiar and different absorption curve (b) when laurylbetaine is added to bilirubin. From this, it is inferred that the stereochemical structure of bilirubin is altered by the presence of an amphoteric surfactant, and as a result, it becomes difficult for it to serve as a substrate of peroxidase, canceling the competition with a color developer capable of being oxidized. In an assay method in which an amphoteric surfactant and a ferrocyanide are used in combination, these two produce synergical effects to enhance the effect of the invention.

EXAMPLE 1

The samples used were human sera to which bilirubin was added at various predetermined concentrations. The amount of uric acid in the samples was determined using reagents for assaying uric acid formulated as shown in Table 1, and the effect of bilirubin was investigated.

TABLE 1

|  | Comp. Examples | | | Invention Examples | | |
| --- | --- | --- | --- | --- | --- | --- |
|  | 1 | 2 | 3 | 1 | 2 | 3 |
| First Reagent | | | | | | |
| 2-(N-Morpholino)ethanesulfonic acid | | | | 75 mM | | |
| N-Ethyl-N-(2-hydroxy-3-sulfopropyl)-m-toluidine | | | | 0.75 mM | | |
| Peroxidase | | | | 3.0 u/ml | | |
| Bovine serum albumin | 0.1 wt % | — | — | — | — | — |
| Alkylbetaine[1] | — | — | — | 0.39 wt % | — | — |
| Alkylamide betaine[2] | — | — | — | — | 0.45 wt % | — |
| Alkylimidazolium betaine[3] | — | — | — | — | — | 0.87 wt % |
| Second reagent | | | | | | |
| 2-(N-Morpholino)ethanesulfonic acid | | | | 75 mM | | |
| 4-Aminoantipyrine | | | | 0.75 mM | | |
| uricase | | | | 0.6 u/ml | | |
| Potassium ferrocyanide | — | | | 0.015 mM | | |

In Table 1, the numerals are concentrations in reagents.
[1] Anhitol 24B (Kao)
[2] Enagycol C-30B (Lion)
[3] Anhitol 20Y (Kao)

ASSAY METHOD

A first reagent (260 μl) was added to a sample (70 μl) and the mixture was stirred. The mixture was then heated at 37° C. for 5 minutes. Absorption at a wave length of 546 nm was measured using a blank (no reagent) as a control (absorption I).

Thereafter, a second reagent (130 μl) was further added to the mixture and heated at 37° C. for 5 minutes. Absorption at a wave length of 546 nm was measured using a blank (no reagent) as a control (absorption II). As the blanks, purified water was used. From the thus obtained absorptions I and II, absorption of the sample was calculated according to the following equation:

Absorption of the sample = absorption II −

$$\left[ \text{absorption I} \times \frac{\text{volume of sample} + \text{volume of 1st } R}{\text{volume of sample} + \text{volume of 1st } R + \text{volume of 2nd } R} \right]$$

(R stands for "reagent").

Uric acid solutions of known concentrations were also treated in a similar manner as described above, and their absorptions were calculated. The results were compared with the absorption of the sample, and the uric acid concentration of the sample was obtained.

RESULTS

The results are shown in Table 2. As is apparent from Table 2, conventional methods in which nothing was added (Comparative Example 1), potassium ferrocyanide alone was added (Comparative Example 2) or potassium ferrocyanide and bovine serum albumin were added in combination (Comparative Example 3) presented considerably low results of measurements as the amounts of bilirubin in the samples increased. By contrast, in the assay methods of the present invention in which potassium ferrocyanide and an amphoteric surfactant were used in combination (Invention Examples 1 to 3), interference by bilirubin was quite successfully eliminated.

TABLE 2

| Concentration of bilirubin in samples (mg/dl) | Measurements of uric acid (mg/dl) | | | | | |
| --- | --- | --- | --- | --- | --- | --- |
|  | Comp. Examples | | | Invention Examples | | |
|  | 1 | 2 | 3 | 1 | 2 | 3 |
| 0 | 4.5 | 4.4 | 4.3 | 4.4 | 4.5 | 4.5 |
| 5 | 2.1 | 4.0 | 4.0 | 4.4 | 4.5 | 4.3 |
| 10 | 1.1 | 3.6 | 3.6 | 4.4 | 4.4 | 4.3 |
| 15 | 0.7 | 3.2 | 3.2 | 4.3 | 4.3 | 4.2 |
| 20 | 0.5 | 2.8 | 2.9 | 4.2 | 4.3 | 4.2 |
| 30 | 0.4 | 2.1 | 2.3 | 4.1 | 4.2 | 4.0 |
| 50 | 0.3 | 1.1 | 1.5 | 4.0 | 4.0 | 3.8 |

EXAMPLE 2

The procedure of Example 1 (measurements of uric acid) was repeated except that the various surfactants shown in Table 3 were used in place of the surfactants in Table 1, and 0.5% by weight of each surfactant was added to both first and second reagents. The performance of the surfactants in eliminating interference by bilirubin was compared.

The results are shown in Table 3. The standards for the evaluation of effect shown in Table 3 were as follows.

STANDARDS

The evaluation was based on the difference between the uric acid measurement obtained when the concentration of bilirubin in the sample was 0 mg/dl and that obtained when the concentration of bilirubin in the sample was 50 mg/dl.

| | |
| --- | --- |
| 0 to 0.5: | A |
| 0.6 to 1.0: | B |
| 1.1 to 3.0: | C |
| 3.1 or more: | D |

As is apparent from Table 3, the amphoteric surfactant was remarkably superior to other types of surfactants in eliminating interference of bilirubin.

TABLE 3

| Surfactants | Measurements of uric acid (mg/dl) | | Evaluation of effect |
|---|---|---|---|
| | bilirubin conc. = 0 mg/dl | bilirubin conc. = 50 mg/dl | |
| (not added) | 4.4 | 1.5 | D |
| Amphoteric surfactant: | | | |
| laurylbetaine | 4.7 | 4.3 | A |
| Anionic surfactants: | | | |
| triethanolamine laurylsulfate | 3931.1 | 1378.3 | D |
| ammonium laurylsulfate | could not be measured | | D |
| sodium alkylnaphthalene sulfonate | 3055.4 | 1528.9 | D |
| sodium polyoxyethylene laurylether sulfate | 21.4 | 4.5 | D |
| sodium polyoxyethylene alkylether sulfate | 4.5 | 1.7 | D |
| triethanolamine polyoxyethylene alkylether sulfate | 14.7 | 0.5 | D |
| sodium polyoxyethylene alkylphenylether sulfate | 30.0 | 5.4 | D |
| Cationic surfactant: | | | |
| Cetyltrimethylammonium chloride | −5.1 | −6.7 | D |
| Nonionic surfactants: | | | |
| polyoxyethylene lauryl ether | 4.4 | 3.2 | C |
| polyoxyethylene oleyl ether | 4.3 | 1.0 | D |
| polyoxyethylene higher alcohol ether | 50.3 | 45.2 | D |
| polyoxyethylene nonylphenyl ether | 4.5 | 3.4 | C |
| polyoxyethylene derivative | 4.4 | 3.2 | C |
| tetraoleic acid polyoxyethylene sorbitol | 4.5 | 2.0 | C |

EXAMPLE 3

The samples used were human sera to which bilirubin was added at various predetermined concentrations. In a similar manner to that described in Example 2, triglyceride was assayed using the reagents formulated as shown in Table 4, and the effect of bilirubin was investigated.

The results are shown in Table 5.

TABLE 4

| | Comp. Example | Invention Examples | |
|---|---|---|---|
| | 4 | 4 | 5 |
| First Reagents | | | |
| 2-(N-Morpholino)-ethanesulfonic acid | 200 mM | 200 mM | 200 mM |
| Glycerokinase | 0.9 u/ml | 0.9 u/ml | 0.9 u/ml |
| Glycero-3-phosphate oxidase | 3.75 u/ml | 3.75 u/ml | 3.75 u/ml |
| Peroxidase | 1.95 u/ml | 1.95 u/ml | 1.95 u/ml |
| Sodium 3,5-dimethoxy-N-ethyl-N-(2-hydroxy-3-sulfopropyl)aniline | 1.75 mM | 1.75 mM | 1.75 mM |
| Alkylbetaine[1] | — | 0.26 wt % | — |
| Alkylimidazolium betaine[2] | — | — | 0.29 wt % |

TABLE 4-continued

| | Comp. Example | Invention Examples | |
|---|---|---|---|
| | 4 | 4 | 5 |
| Second Reagents | | | |
| 2-(N-Morpholino)-ethanesulfonic acid | 200 mM | 200 mM | 200 mM |
| 4-Aminoantipyrine | 1.5 mM | 1.5 mM | 1.5 mM |
| Lipoprotein lipase | 900 u/ml | 900 u/ml | 900 u/ml |
| Alkylbetaine[1] | — | 0.26 wt % | — |
| Alkylimidazolium betaine[2] | — | — | 0.29 wt % |
| Potassium ferrocyanide | 7.5 μM | 7.5 μM | 7.5 μM |

In Table 4, the numerals are concentrations in reagents.
[1] Anhitol 24B (Kao)
[2] Anhitol 20Y (Kao)

TABLE 5

| Bilirubin concentration in samples (mg/dl) | Measurements of triglyceride (mg/dl) | | |
|---|---|---|---|
| | Comp. Ex. 4 | Invention Ex. 4 | Invention Ex. 5 |
| 0 | 93 | 93 | 93 |
| 10 | 87 | 92 | 92 |
| 20 | 71 | 92 | 92 |
| 30 | 59 | 91 | 93 |
| 50 | 46 | 92 | 90 |

As is apparent from Table 5, the conventional method (Comparative Example 4) gave low values of measurements as the amount of bilirubin in the sample increased, whereas the methods of the present invention (Invention Examples 4 and 5) in which potassium ferrocyanide and an amphoteric surfactant were used successfully eliminated interference of bilirubin.

EXAMPLE 4

The samples used were human sera to which bilirubin was added at various predetermined concentrations. In a similar manner to that described in Example 2, total cholesterol was assayed using the reagents formulated as shown in Table 6, and the effect of bilirubin was investigated.

The results are shown in Table 7.

TABLE 6

| | Comp. Example | Invention Examples | |
|---|---|---|---|
| | 5 | 6 | 7 |
| First Reagents | | | |
| Potassium hydrogenphthalate | 60 mM | 60 mM | 60 mM |
| 4-Aminoantipyrine | 2.3 mM | 2.3 mM | 2.3 mM |
| Cholesterol esterase | 0.3 u/ml | 0.3 u/ml | 0.3 u/ml |
| Peroxidase | 4.5 u/ml | 4.5 u/ml | 4.5 u/ml |
| Alkylbetaine[1] | — | 0.26 wt % | — |
| Alkylamine oxide[2] | — | — | 0.53 wt % |
| Second Reagents | | | |
| Potassium | 60 mM | 60 mM | 60 mM |
| Sodium 3,5-dimethoxy-N-ethyl-N-(2-hydroxy- | 0.6 mM | 0.6 mM | 0.6 mm |

TABLE 6-continued

| | Comp. Example | Invention Examples | |
|---|---|---|---|
| | 5 | 6 | 7 |
| 3-sulfopropyl)aniline Cholesterol esterase | 0.7 u/ml | 0.7 u/ml | 0.7 u/ml |
| Alkylbetaine[1] | — | 0.26 wt % | — |
| Alkylamine oxide[2] | — | — | 0.53 wt % |
| Potassium ferrocyanide | 7.5 μM | 7.5 μM | 7.5 μM |

In Table 6, the numerals are concentrations in reagents.
[1]Anhitol 24B (Kao)
[2]Anhitol 20N (Kao)

TABLE 7

| Bilirubin concentration | Measurements of T. cholesterol (mg/dl) | | |
|---|---|---|---|
| in samples (mg/dl) | Comp. Ex. 5 | Invention Ex. 6 | Invention Ex. 7 |
| 0 | 169 | 168 | 168 |
| 10 | 154 | 165 | 166 |
| 15 | 148 | 167 | 169 |
| 20 | 142 | 166 | 165 |
| 30 | 132 | 166 | 169 |
| 50 | 110 | 166 | 166 |

As is apparent from Table 7, the conventional method (Comparative Example 5) gave low values of measurements as the amount of bilirubin in the sample increased, whereas the methods of the present invention (Invention Examples 6 and 7) in which potassium ferrocyanide and an amphoteric surfactant were used successfully eliminated interference of bilirubin.

According to the assay method of the present invention, even when the biological component to be detected is present in a trace amount, the interference of bilirubin can be effectively eliminated in assays of biological components in which peroxidase generated from an enzymatic reaction is detected using peroxidase and a color developer capable of being oxidized.

We claim:

1. An assay method for biological components in a biological sample comprising at least the following first step (A), second step (B) and third step (C):

Step A: (i) a reaction step for generating a substrate of oxidase, or (ii) a reaction step for obtaining a blank value of a sample;

Step B: a reaction step for initially generating hydrogen peroxides through oxidase reaction and then detecting the generated hydrogen peroxides with peroxidase and a color developer capable of being oxidized; wherein Step (A) is carried out in the presence of amphoteric surfactant and in the absence of ferrocyanide, and Step (B) is carried out either in the presence of ferrocyanide or in the presence of amphoteric surfactant and ferrocyanide; and Step C: a step for correlating the amount of color developed to the amount of biological components in the biological sample.

2. An assay method for colorimetric determination of biological components in a biological sample comprising at least the following first step (A) and second step (B), wherein (A) comprises, in the presence of amphoteric surfactant and in the absence of ferrocyanide, generating a substrate of oxidase; and (B) comprises, in the presence of ferrocyanide or in the presence of amphoteric surfactant and ferrocyanide, initially generating hydrogen peroxide through oxidase reaction on said substrate of oxidase and then detecting the generated hydrogen peroxide with peroxidase and a color developer capable of being oxidized in the presence of amphoteric surfactant and ferrocyanide, and correlating the amount of color developed to the amount of biological components in the biological sample.

3. The assay method according to claim 2, wherein the amphoteric surfactant is selected from the group consisting of alkylimidazolium betaines, alkyl betaines, alkylamide betaines, alkylalanines, and alkylamine oxides and mixtures thereof.

4. The assay method according to claim 2, wherein the color developer is 4-aminophenazone and a hydrogen donor in combination.

5. The assay method according to claim 2, wherein the biological component is a component of blood or urine.

6. The assay method according to claim 2, wherein the amphoteric surfactant and the ferrocyanide are present, during detection of the biological component, from 0.01 to 10 wt. % and from 1 to 100 μM.

7. The assay method according to claim 2, wherein the biological components in the biological sample are trace components.

8. The assay method according claim 6, wherein the ferrocyanide is present in the amount of 5 to 50 μM.

9. The assay method according to claim 6, wherein the amphoteric surfactant and the ferrocyanide are present, during detection of the biological component, from 0.1 to 5 wt. % and from 5 to 50 μM, respectively.

10. The assay method according to claim 2, wherein the biological components are selected from the group consisting of triglyceride, glucose, phospholipids, total cholesterol, free fatty acids, uric acid, cholinesterase, creatinine and creatine.

11. The assay method according to claim 10, wherein the phospholipids are selected from the group consisting of lecithin, sphingomyelin and lysolecithin.

12. In a colorimetric assay method for biological components co-existing with bilirubin in a biological sample, in which an enzyme is reacted with the biological components to generate hydrogen peroxide and the hydrogen peroxide is reacted with a color developer capable of being oxidized in the presence of peroxidase, wherein the improvement comprises avoiding interference by bilirubin by (A) generating a substrate of oxidase in the presence of amphoteric surfactant and in the absence of ferrocyanide, and (B) generating hydrogen peroxide through oxidase reaction on said substrate of oxidase in the presence of ferrocyanide or in the presence of amphoteric surfactant and ferrocyanide, and correlating the amount of color developed to the amount of biological components in the biological sample.

13. The assay for triglycerides according to claim 12, wherein triglycerides in a biological sample are reacted with lipoprotein lipase to form glycerol, which is reacted with glycerokinase to form glycerol-3-phosphate, which is reacted with glycerol-3-phosphate oxidase to generate hydrogen peroxide.

14. The assay for glucose according to claim 12, wherein glucose in a biological sample is reacted with glucose oxidase to generate hydrogen peroxide.

15. The assay for phospholipids according to claim 12, wherein phospholipids in a biological sample are reacted with phospholipase D to form choline, which is reacted with choline oxidase to generate hydrogen peroxide.

16. The assay for total cholesterol according to claim 12, wherein ester-type cholesterol in a biological sample is reacted with cholesterol esterase to form free cholesterol, which is reacted with cholesterol oxidase to generate hydrogen peroxide.

17. The assay for free fatty acid according to claim 12, wherein free fatty acid in a biological sample and CoA are reacted with acyl CoA synthetase to form acyl CoA, which is reacted with acyl CoA oxidase to generate hydrogen peroxide.

18. The assay for uric acid according to claim 12, wherein uric acid in a biological sample is reacted with uricase to generate hydrogen peroxide.

19. The assay for cholinesterase according to claim 12, wherein benzoylcholine in a biological sample is reacted with cholinesterase to form choline, which is reacted with choline oxidase to generate hydrogen peroxide.

20. The assay for creatinine according to claim 12, wherein creatinine in a biological sample is reacted with creatininase to form creatine, which is reacted with creatinase to form sarcosine, which is reacted with sarcosine oxidase to generate hydrogen peroxide.

\* \* \* \* \*